(12) United States Patent
Olstowski

(10) Patent No.: US 7,244,395 B2
(45) Date of Patent: Jul. 17, 2007

(54) APPARATUS FOR TRACE SULFUR DETECTION USING UV FLUORESCENCE

(75) Inventor: Franek Olstowski, Houston, TX (US)

(73) Assignee: Petroleum Analyzer Company, LP, Houston, TX (US)

( * ) Notice: Subject to any disclaimer, the term of this patent is extended or adjusted under 35 U.S.C. 154(b) by 0 days.

(21) Appl. No.: 10/674,269

(22) Filed: Sep. 29, 2003

(65) Prior Publication Data

US 2005/0074365 A1  Apr. 7, 2005

(51) Int. Cl.
*G01N 31/12* (2006.01)
(52) U.S. Cl. .................... 422/80; 422/91; 436/123; 436/175
(58) Field of Classification Search .............. 422/80, 422/91; 436/123, 160, 172, 175
See application file for complete search history.

(56) References Cited

U.S. PATENT DOCUMENTS

| | | | | |
|---|---|---|---|---|
| 4,569,918 A | * | 2/1986 | Moore et al. | 436/122 |
| 5,152,963 A | * | 10/1992 | Wreyford | 422/80 |
| 5,531,105 A | * | 7/1996 | Leong et al. | 73/116 |
| 5,567,623 A | * | 10/1996 | Rounbehler et al. | 436/158 |
| 6,830,730 B2 | * | 12/2004 | Rhodes | 422/78 |

* cited by examiner

*Primary Examiner*—Lyle A. Alexander
(74) *Attorney, Agent, or Firm*—Robert W Strozier

(57) ABSTRACT

A method and system for performing low level sulfur UV fluorescence measures including an UV interference reduction system which removes or destroys interfering nitrogen oxides. The preferred nitrogen removal systems include introducing ozone into the system in sufficient quantities to destroy any produce NO and optionally a nitrogen sparge or similar nitrogen gas removal system.

14 Claims, 16 Drawing Sheets

File Name: Soctrade.sam
Curr. Cal File: As2551 cal
Orig. Cal File: As2551 cal
Calibration based on: Total Counts
Blank Correction is: OFF
Comments: Test UV Fluorescence Detector for Soctrade
Version 3.7.7 6/28/02

| Name | Use S | SConc | SCnts | S%RSD | Divider | Multiplier | Time | Date | OpID | Tray # | Vial Pos |
|---|---|---|---|---|---|---|---|---|---|---|---|
| 1ppm/i-C8 | X | 0.629 | 23472.3 | 1.9 | | | 2:13PM | 3/11/03 | LJN | 1 | 1 |
| 1ppm/i-C8.1 | X | 0.627 | 23690.0 | | 1.00 | 1.00 | 2:19PM | 3/11/03 | LJN | | |
| 1ppm/i-C8.2 | X | 0.645 | 24202.4 | | 1.00 | 1.00 | 2:25PM | 3/11/03 | LJN | | |
| 1ppm/i-C8.3 | X | 0.618 | 23430.0 | | 1.00 | 1.00 | 2:31PM | 3/11/03 | LJN | | |
| 1ppm/i-C8.4 | X | 0.628 | 23729.2 | | 1.00 | 1.00 | 2:37PM | 3/11/03 | LJN | | |
| 1ppm/i-C8.5 | X | 0.626 | 23660.1 | | 1.00 | 1.00 | | | | | |
| Blank/i-C8 | X | -0.151 | 1465.7 | 15.40 | | | 2:44PM | 3/11/03 | LJN | 1 | 1 |
| Blank/i-C8.1 | X | -0.148 | 1561.1 | | 1.00 | 1.00 | 2:50PM | 3/11/03 | LJN | | |
| Blank/i-C8.2 | X | -0.150 | 1512.4 | | 1.00 | 1.00 | 2:56PM | 3/11/03 | LJN | | |
| Blank/i-C8.3 | X | -0.141 | 1768.8 | | 1.00 | 1.00 | 3:02PM | 3/11/03 | LJN | | |
| Blank/i-C8.4 | X | -0.160 | 1214.1 | | 1.00 | 1.00 | 3:08pm | 3/11/03 | LJN | | |
| Blank/i-C8.5 | X | -0.158 | 1272.2 | | 1.00 | 1.00 | | | | | |
| 500ppmN-Dl | X | 0.744 | 27020.0 | N/A | 1.00 | 1.00 | 3:16PM | 3/11/03 | LJN | 1 | 1 |
| i-C3OH | X | -0.173 | 852.5 | N/A | 1.00 | 1.00 | 3:39PM | 3/11/03 | LJN | 1 | 1 |
| Toluene | X | -0.120 | 2359.6 | N/A | 1.00 | 1.00 | 4:15PM | 3/11/03 | LJN | 1 | 1 |
| MeOH | X | -0.190 | 350.5 | N/A | 1.00 | 1.00 | 4:48PM | 3/11/03 | LJN | 1 | 1 |

FIG. 4

File Name: O3 addition.sam
Curr. Cal File: Interference.cal
Orig. Cal File: Interference.cal
Calibration based on: Total Counts
Blank Correction is: OFF
Comments: All Ozone (O3) Addition = 1cc/min O2 with ATOMIC Prototype
(Hv Transformer Primary @7vdc)
All 50ppbS standards in Fisher i-C8
Version: 3.7.7  6/28/02

| Name | Use S | SConc | SCnts | SSDev | S%RSD | Divider | Multiplier | Time | Date |
|---|---|---|---|---|---|---|---|---|---|
| Reidel +O3 | X | NaN | 16.6 | 15.77 | 95.12 | | | | |
| Reidel +O3.1 | X | Inf | 37.6 | | | 1.00 | 1.00 | 11:08 PM | 4/23/03 |
| Reidel +O3.2 | X | Inf | 12.2 | | | 1.00 | 1.00 | 11:12 PM | 4/23/03 |
| Reidel +O3.3 | X | Inf | 28.1 | | | 1.00 | 1.00 | 11:16 PM | 4/23/03 |
| Reidel +O3.4 | X | -Inf | 0.9 | | | 1.00 | 1.00 | 11:20 PM | 4/23/03 |
| Reidel +O3.5 | X | -Inf | 4.2 | | | 1.00 | 1.00 | 11:24 PM | 4/23/03 |
| 50ppb+O3 | X | Inf | 355.9 | 81.09 | 22.79 | | | | |
| 50ppb+O3.1 | X | Inf | 429.9 | | | 1.00 | 1.00 | 11:29 PM | 4/23/03 |
| 50ppb+O3.2 | X | Inf | 442.9 | | | 1.00 | 1.00 | 11:33 PM | 4/23/03 |
| 50ppb+O3.3 | X | Inf | 287.1 | | | 1.00 | 1.00 | 11:37 PM | 4/23/03 |
| 50ppb+O3.4 | X | Inf | 263.5 | | | 1.00 | 1.00 | 11:41 PM | 4/23/03 |
| 50ppb+O3.5 | X | Inf | 355.9 | | | 1.00 | 1.00 | 11:45 PM | 4/23/03 |
| Reidel +O3 | X | NaN | 5.6 | 5.49 | 97.56 | | | | |
| Reidel +O3.1 | X | -Inf | 0.0 | | | 1.00 | 1.00 | 12:03 PM | 4/23/03 |
| Reidel +O3.2 | X | -Inf | 6.4 | | | 1.00 | 1.00 | 12:07 PM | 4/23/03 |
| Reidel +O3.3 | X | -Inf | 5.1 | | | 1.00 | 1.00 | 12:11 PM | 4/23/03 |

FIG. 8A

| Name | Use S | SConc | SCnts | SSDev | S%RSD | Divider | Multiplier | Time | Date |
|---|---|---|---|---|---|---|---|---|---|
| Reidel +03.4 | X | -Inf | 2.2 | | | 1.00 | 1.00 | 12:15 PM | 4/23/03 |
| Reidel +03.5 | X | -Inf | 14.4 | | | 1.00 | 1.00 | 12:19 PM | 4/23/03 |
| Fisher+03 | X | NaN | 18.3 | 15.49 | 84.65 | | | | |
| Fisher+03.1 | X | Inf | 28.6 | | | 1.00 | 1.00 | 12:24 PM | 4/23/03 |
| Fisher+03.2 | X | -Inf | 4.3 | | | 1.00 | 1.00 | 12:28 PM | 4/23/03 |
| Fisher+03.3 | X | -Inf | 0.0 | | | 1.00 | 1.00 | 12:32 PM | 4/23/03 |
| Fisher+03.4 | X | Inf | 35.6 | | | 1.00 | 1.00 | 12:36 PM | 4/23/03 |
| Fisher+03.5 | X | Inf | 23.0 | | | 1.00 | 1.00 | 12:40 PM | 4/23/03 |
| 50ppb+03 | X | Inf | 352.9 | 46.42 | 13.16 | | | | |
| 50ppb+03.1 | X | Inf | 313.8 | | | 1.00 | 1.00 | 12:45 PM | 4/23/03 |
| 50ppb+03.2 | X | Inf | 317.1 | | | 1.00 | 1.00 | 12:49 PM | 4/23/03 |
| 50ppb+03.3 | X | Inf | 337.3 | | | 1.00 | 1.00 | 12:53 PM | 4/23/03 |
| 50ppb+03.4 | X | Inf | 370.6 | | | 1.00 | 1.00 | 12:57 PM | 4/23/03 |
| 50ppb+03.5 | X | Inf | 425.4 | | | 1.00 | 1.00 | 1:01 PM | 4/23/03 |
| 1ppm+03 | X | Inf | 9816.3 | 118.67 | 1.21 | | | | |
| 1ppm+03.1 | X | Inf | 9657.6 | | | 1.00 | 1.00 | 1:21 PM | 4/23/03 |
| 1ppm+03.2 | X | Inf | 9871.8 | | | 1.00 | 1.00 | 1:25 PM | 4/23/03 |
| 1ppm+03.3 | X | Inf | 9761.8 | | | 1.00 | 1.00 | 1:29 PM | 4/23/03 |
| 1ppm+03.4 | X | Inf | 9815.8 | | | 1.00 | 1.00 | 1:33 PM | 4/23/03 |
| 1ppm+03.5 | X | Inf | 9974.7 | | | 1.00 | 1.00 | 1:37 PM | 4/23/03 |
| 50ppb+03 | X | Inf | 332.7 | 71.52 | 21.50 | | | | |
| 50ppb+03.1 | X | Inf | 245.3 | | | 1.00 | 1.00 | 1:43 PM | 4/23/03 |
| 50ppb+03.2 | X | Inf | 363.7 | | | 1.00 | 1.00 | 1:47 PM | 4/23/03 |
| 50ppb+03.3 | X | Inf | 270.8 | | | 1.00 | 1.00 | 1:51 PM | 4/23/03 |
| 50ppb+03.4 | X | Inf | 414.5 | | | 1.00 | 1.00 | 1:55 PM | 4/23/03 |
| 50ppb+03.5 | X | Inf | 369.2 | | | 1.00 | 1.00 | 1:59 PM | 4/23/03 |

*FIG. 8B*

| Name | Use S | SConc | SCnts | SSDev | S%RSD | Divider | Multiplier | Time | Date |
|---|---|---|---|---|---|---|---|---|---|
| F-Nozone | | | | | | | | | |
| F-Nozone.1 | X | Inf | 963.5 | 48.85 | 5.07 | 1.00 | 1.00 | 2:29 PM | 4/23/03 |
| F-Nozone.2 | X | Inf | 960.1 | | | 1.00 | 1.00 | 2:33 PM | 4/23/03 |
| F-Nozone.3 | X | Inf | 919.6 | | | 1.00 | 1.00 | 2:37 PM | 4/23/03 |
| F-Nozone.4 | X | Inf | 917.3 | | | 1.00 | 1.00 | 2:41 PM | 4/23/03 |
| F-Nozone.5 | X | Inf | 1033.7 | | | 1.00 | 1.00 | 2:45 PM | 4/23/03 |
| | X | Inf | 986.9 | | | 1.00 | 1.00 | | |
| 50ppb Nozone | X | Inf | 1212.0 | 127.80 | 10.54 | | | | |
| 50ppb Nozone.1 | X | Inf | 1133.6 | | | 1.00 | 1.00 | 2:57 PM | 4/23/03 |
| 50ppb Nozone.2 | X | Inf | 1378.7 | | | 1.00 | 1.00 | 3:01 PM | 4/23/03 |
| 50ppb Nozone.3 | X | Inf | 1321.0 | | | 1.00 | 1.00 | 3:05 PM | 4/23/03 |
| 50ppb Nozone.4 | X | Inf | 1107.7 | | | 1.00 | 1.00 | 3:09 PM | 4/23/03 |
| 50ppb Nozone.5 | X | Inf | 1119.1 | | | 1.00 | 1.00 | 3:13 PM | 4/23/03 |
| 1ppm-Nozone | X | Inf | 11311.0 | 83.00 | 0.73 | | | | |
| 1ppm-Nozone.1 | X | Inf | 112068 | | | 1.00 | 1.00 | 3:18 PM | 4/23/03 |
| 1ppm-Nozone.2 | X | Inf | 11363.2 | | | 1.00 | 1.00 | 3:22 PM | 4/23/03 |
| 1ppm-Nozone.3 | X | Inf | 11306.4 | | | 1.00 | 1.00 | 3:26 PM | 4/23/03 |
| 1ppm-Nozone.4 | X | Inf | 11260.6 | | | 1.00 | 1.00 | 3:30 PM | 4/23/03 |
| 1ppm-Nozone.5 | X | Inf | 11417.8 | | | 1.00 | 1.00 | 3:34 PM | 4/23/03 |

FIG. 8C

APPARATUS FOR TRACE SULFUR DETECTION USING UV FLUORESCENCE

BACKGROUND OF THE INVENTION

1. Field of the Invention

The present invention relates to a method and apparatus for improving the detection of trace amounts of total sulfur in fluids such as fuels and petroleum distillates using UV fluorescence.

More particularly, the present invention relates to a method and apparatus for improving the detection of trace amounts of total sulfur in fluids such as fuels and petroleum distillates using UV fluorescence, where the method and apparatus involve removing and/or chemically deactivating interfering nitrogen species prior to UV fluorescence detection of sulfur.

2. Description of the Related Art

For the most part, detection of sulfur by UV fluorescence is normally considered to be relatively free of any significant interference from complete oxidation of most hydrocarbon samples and combustion byproducts. However, it has been noted that when analyzing iso-octane blanks or low-level sulfur samples, higher than expected sulfur readings are routinely encountered with UV fluorescence methods when compared to data acquired from other equally effective analytical methods such as lead-acetate tape instrumentation. There have been numerous theories behind this discrepancy, but until now, a satisfactorily credible explanation has remained elusive.

Although the UV fluorescent instruments include calibration software routines that can subtract "blank counts" or constant values from analyzed samples, frequently such offsetting changes whenever a combustion tube or gas supply bottle is changed. Recently, exceptionally high "background" counts relative to what would be expected have been noted. Moreover, it has also been noted that water samples create "no background," while alcohols show increased "background" counts as the molecular weight of the alcohol increases.

Thus, there is a need in the art for an improved UV fluorescent apparatus and associated method for trace sulfur detection that is substantially free of a hereto unknown source of interference.

SUMMARY OF THE INVENTION

The present invention provides an apparatus for improving total sulfur analysis in a sample containing trace amounts of sulfur using UV fluorescence, where the apparatus includes a UV fluorescence sulfur instrument having an UV interference reduction unit, which includes removing trace nitrogen oxide precursors and/or chemically removing or eliminating interfering nitrogen oxide species prior to or during UV detection of sulfur species.

The present invention also provides an apparatus for improving the detection of trace amounts of total sulfur in a sample using UV fluorescence, where the apparatus includes a sample inlet, an oxidizing agent inlet, a combustion zone, an UV interference reduction system and a UV detection system.

The present invention also provides an apparatus for improving the detection of trace amounts of total sulfur in a sample using UV fluorescence, where the apparatus includes a sample inlet, an oxidizing agent inlet, a combustion zone, an UV interference reduction system and a UV detection system, where the interference reduction system comprises an ozone generator and at least one ozone inlet.

The present invention also provides an apparatus for improving the detection of trace amounts of total sulfur in a sample using UV fluorescence, where the apparatus includes a sample inlet, an oxidizing agent inlet, a combustion zone, an UV interference reduction system, and a UV detection system, where the interference reduction system comprises at least one nitrogen gas sparge unit, an ozone generator and at least one ozone inlet.

The present invention provides a method for improving the detection of trace amounts of total sulfur in fluids such as fuels and petroleum distillates using UV fluorescence, where the method includes a step designed to reduce interfering UV fluorescence from nitrogen species in the sample, oxidizing agent, or inadvertently introduced into the apparatus prior to or during UV fluorescence detection of sulfur in the sample.

DESCRIPTION OF THE DRAWINGS

The invention can be better understood with reference to the following detailed description together with the appended illustrative drawings in which like elements are numbered the same:

FIG. 4 is a Table of data of samples run on a conventional instrument, one an UV interference reduction system;

FIGS. 8A-C is a Table of data of samples run on an instrument with an UV interference reduction system.

DETAILED DESCRIPTION OF THE INVENTION

The inventor has found that a sulfur UV fluorescent instrument can be constructed that reduces or substantially eliminates a hitherto unknown source of interference with sulfur UV fluorescence detection of trace sulfur (amounts below about 50 ppb (part per billion)), where the instrument is a conventional instrument incorporating an UV interference reduction system that removes trace amounts of nitrogen gas in feed streams and/or converts interfering nitrogen species into non-interfering nitrogen species prior to UV fluorescence detection of sulfur.

The present invention also provides an apparatus for improving the detection of total sulfur in samples containing trace amounts of sulfur using UV fluorescence, where the apparatus includes a sample inlet, an oxidizing agent inlet, a combustion zone, a UV detection system and an UV interference reduction system. The apparatus can also include a sample supply system.

The present invention provides a method for improving the detection of trace amounts of total sulfur in fluids such as fuels and petroleum distillates using UV fluorescence, where the method includes the step of injecting a sample into an instrument inlet, oxidizing the sample in a combustion zone in the presence of an excess of an oxidizing agent at an elevated temperature and for a time sufficient to completely or substantially completely convert all oxidizable sample components into their corresponding oxides, converting interfering nitrogen species in the sample to non-interfering nitrogen species prior to UV fluorescence detection of sulfur, irradiating the oxides with excitation light and detecting an amount of sulfur present in the sample bases on an amount of fluorescent light emitted by excited sulfur oxides. The method can also include the step of removing trace amount of nitrogen gas ($N_2$) from the sample and/or gases introduced into the system.

Figure 1A:
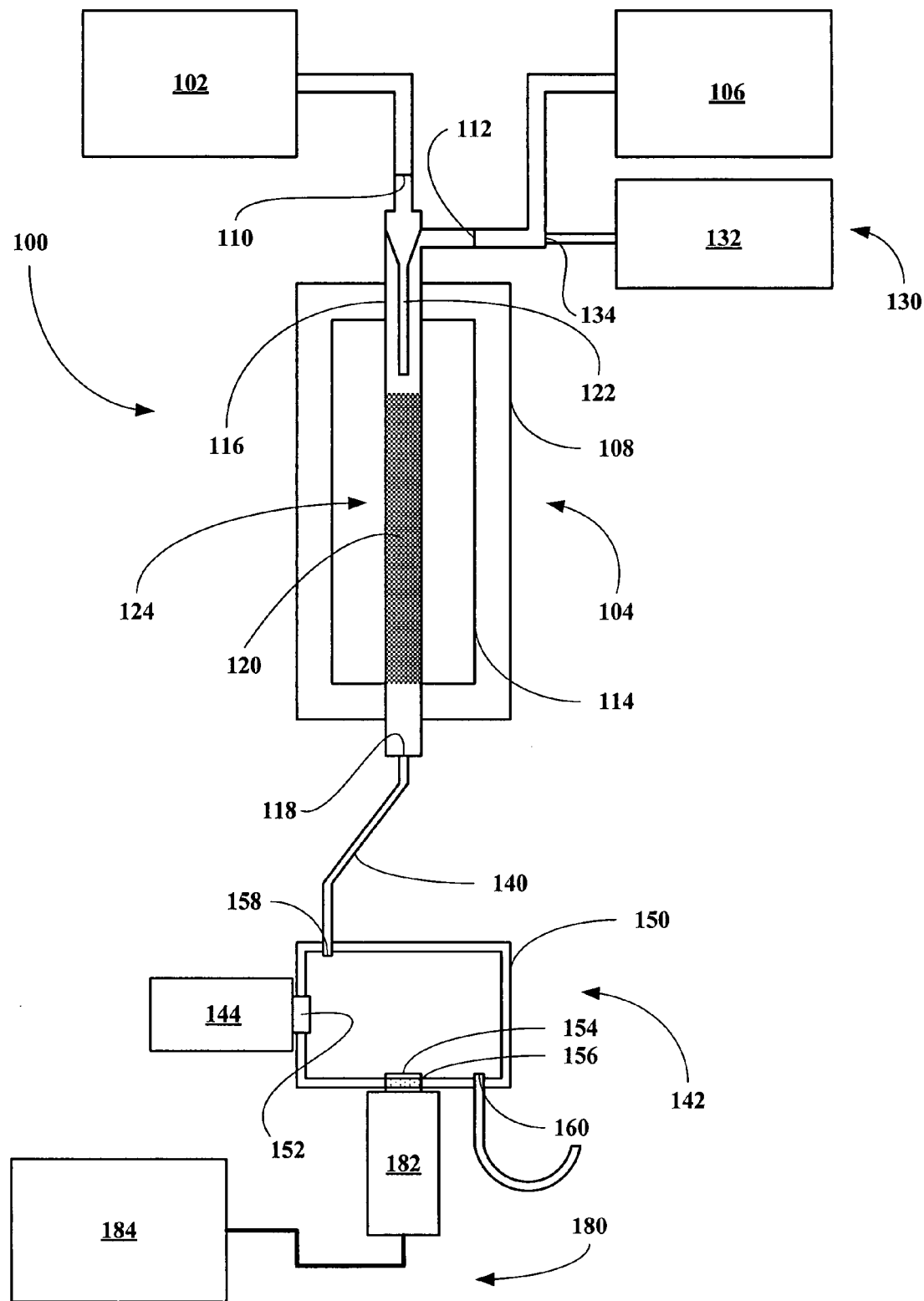
FIG. 1A depicts a block diagrams of a preferred embodiment of an apparatus of this invention including an UV interference reduction system comprising an ozone generator.

Referring now to FIG. 1A, a preferred embodiment of an instrument of this invention, generally 100, is shown to include a sample supply system 102, such as a GC, LC, MPLC, HPLC, electrophoretic separation unit, injection, automated sample injector system, on-line injection systems or other sample supply systems whether separating or non-separating, for introducing a sample into a combustion chamber 104 and an oxidizing agent supply 106 for introducing an oxidizing agent into the combustion chamber 104. The combustion chamber 104 includes a housing 108, a sample inlet 110, an oxidizing agent inlet 112, a heating element 114, a combustion tube 116 and an outlet 118. The combustion tube 116 can also include a packing 120 to improve oxidation efficient and a narrow inlet tube 122 adapted to atomize or nebulize the sample as it enters the combustion zone 124 of the combustion tube 116. The packing material can be any high temperature material such as glass chips, alumina chips, silica chips, silica alumina chips, or any shaped packing for increasing the surface area in the combustion zone. The instrument 100 also includes an UV interference reduction subsystem 130 comprising an ozone generator 132 and an ozone inlet 134 introducing ozone into the combustion tube 116 with the oxidizing agent.

The instrument 100 also includes a transfer tube 140 and a detector system 142 comprising an excitation source 144, an irradiation chamber 150 and a detector/analyzer 180. The irradiation chamber 150 including an excitation light port 152 in optical communication with the excitation source 144, and a fluorescent light port 154 having an optical filter 156 in optical communication with the detector/analyzer 180 and positioned in a direction making an angle with the excitation light to minimize or eliminate excitation light from entering the port 154. Generally, the angle is greater than or equal to ($\geq$) about 45°, preferably, the angle is greater than or equal to ($\geq$) about 60°, particularly, the angle is greater than or equal to ($\geq$) about 80°, and most particularly, the angle is substantially orthogonal to the excitation light port 152, i.e., 90°±5°. The irradiation chamber 150 also includes an oxidized sample inlet 158 and an oxidized sample outlet 160. The detector/analyzer 180 includes a photomultiplier tube (PMT) 182 for detecting fluorescent light and converting the detected light into an electrical output and an analyzer 184 for converting the PMT output into a measure of sulfur concentration in the original sample. The irradiation chamber 150 can also one or more mirrored interior surfaces or inserts having mirrored interior surfaces, where the mirrored surfaces are situated to 1) increase the amount of fluorescent light entering the port 154 and the PMT 182 and/or 2) to increase the amount of excitation light, such be chambers and inserts are described in U.S. Pat. No. 6,075,609 issued 13 Jun. 2000 and U.S. patent application Ser. No. 09/567,339 filed 9 May 2000, incorporated herein by reference.

Figure 1B:
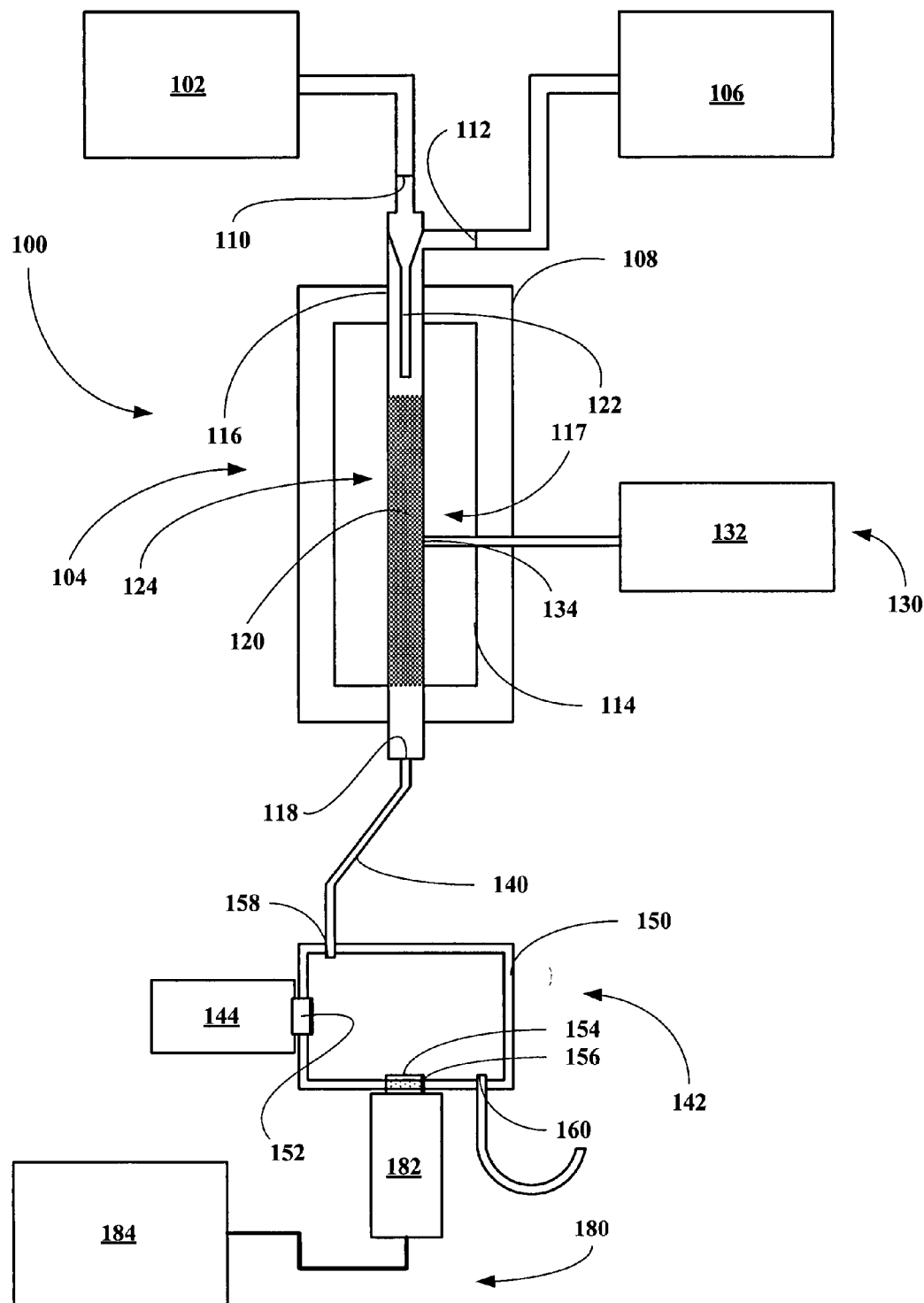
FIG. 1B depicts a block diagrams of another preferred embodiment of an apparatus of this invention including an UV interference reduction system comprising an ozone generator.

Referring now to FIG. 1B, another preferred embodiment of an instrument of this invention, generally 100, is shown to include a sample supply system 102 for introducing a sample into a combustion chamber 104 and an oxidizing agent supply 106 for introducing an oxidizing agent into the combustion chamber 104. The combustion chamber 104 includes a housing 108, a sample inlet 110, an oxidizing agent inlet 112, a heating element 114, a combustion tube 116 and an outlet 118. The combustion tube 116 can also include a packing 120 to improve oxidation efficient and a narrow inlet tube 122 adapted to atomize or nebulize the sample as it enters the combustion zone 124 of the combustion tube 116. The packing material can be any high temperature material such as glass chips, quartz chips, alumina chips, silica chips, silica alumina chips, or any shaped packing for increasing the surface area in the combustion zone that can withstand the temperatures of combustion. The instrument 100 also includes an UV interference reduction subsystem 130 comprising an ozone generator 132 and an ozone inlet 134 introducing ozone into the combustion tube 116 at or near a mid point 117 of the tube 116. The instrument 100 also includes a transfer tube 140 and a detector system 142 comprising an excitation source 144, an irradiation chamber 150 and a detector/analyzer 180. The irradiation chamber 150 including an excitation light port 152 in optical communication with the excitation source 144, and a fluorescent light port 154 having an optical filter 156 in optical communication with the detector/analyzer 180 and positioned in a direction making an angle with the excitation light to minimize or eliminate excitation light from entering the port 154. Generally, the angle is greater than or equal to ($\geq$) about 45°, preferably, the angle is greater than or equal to ($\geq$) about 60°, particularly, the angle is greater than or equal to ($\geq$) about 80°, and most particularly, the angle is substantially orthogonal to the excitation light port 152, i.e., 90°±5°. The irradiation chamber 150 also includes an oxidized sample inlet 158 and an oxidized sample outlet 160. The detector/analyzer 180 includes a photomultiplier tube (PMT) 182 for detecting fluorescent light and converting the detected light into an electrical output and an analyzer 184 for converting the PMT output into a measure of sulfur concentration in the original sample. The irradiation chamber 150 can also one or more mirrored interior surfaces or inserts having mirrored interior surfaces, where the mirrored surfaces are situated to 1) increase the amount of fluorescent light entering the port 154 and the PMT 182 and/or 2) to increase the amount of excitation light, such be chambers and inserts are described in U.S. Pat. No. 6,075,609 issued 13 Jun. 2000 and U.S. patent application Ser. No. 09/567,339 filed 9 May 2000, incorporated herein by reference.

Figure 1C:
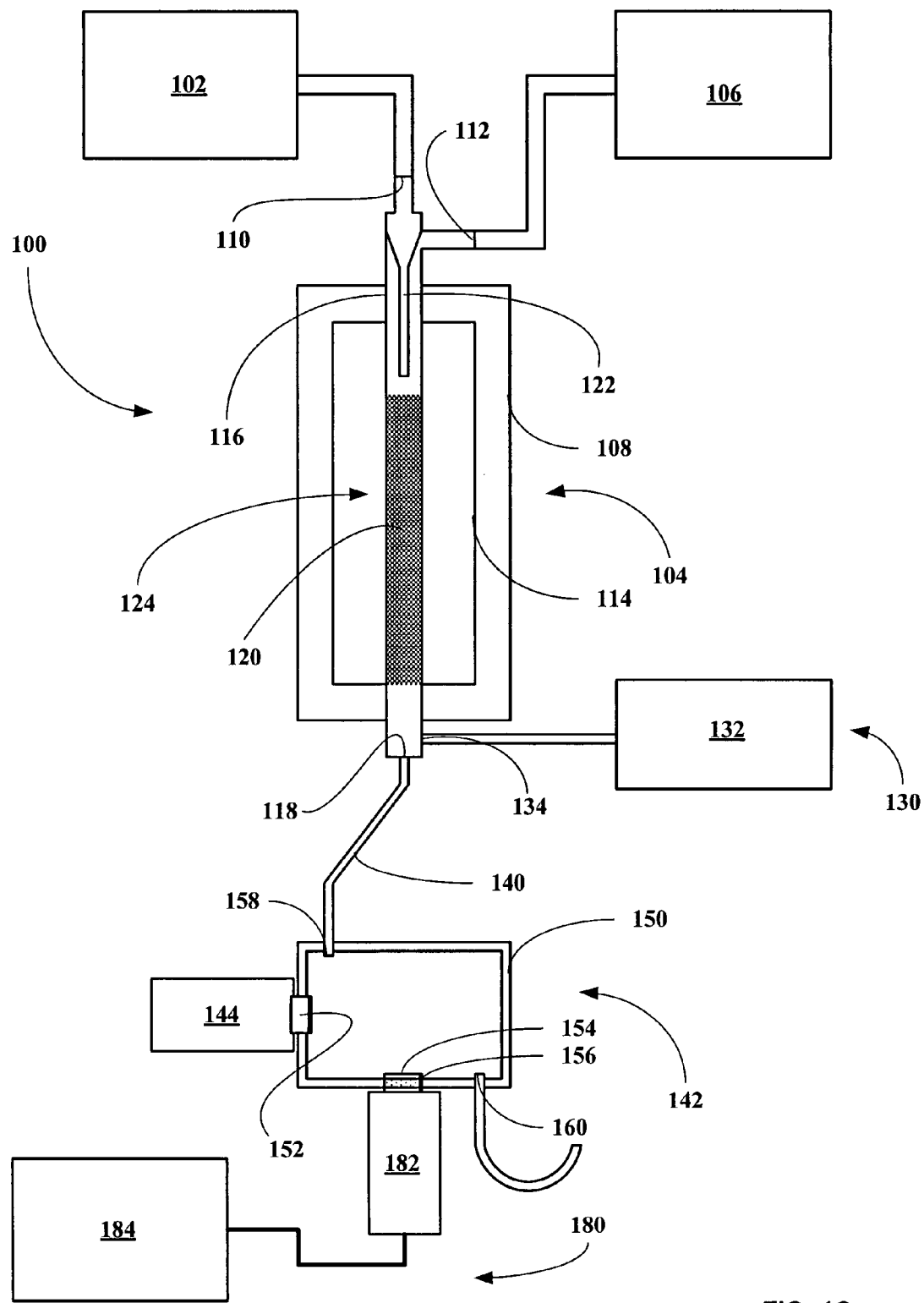
FIG. 1C depicts a block diagrams of another preferred embodiment of an apparatus of this invention including an UV interference reduction system comprising an ozone generator.

Referring now to FIG. 1C, another preferred embodiment of an instrument of this invention, generally 100, is shown to include a sample supply system 102 for introducing a sample into a combustion chamber 104 and an oxidizing agent supply 106 for introducing an oxidizing agent into the combustion chamber 104. The combustion chamber 104 includes a housing 108, a sample inlet 110, an oxidizing agent inlet 112, a heating element 114, a combustion tube 116 and an outlet 118. The combustion tube 116 can also include a packing 120 to improve oxidation efficient and a narrow inlet tube 122 adapted to atomize or nebulize the sample as it enters the combustion zone 124 of the combustion tube 116. The packing material can be any high temperature material such as glass chips, alumina chips, silica chips, silica alumina chips, or any shaped packing for increasing the surface area in the combustion zone. The instrument 100 also includes an UV interference reduction subsystem 130 comprising an ozone generator 132 and an ozone inlet 134 introducing ozone into the combustion tube 116 near the outlet 118. The instrument 100 also includes a transfer tube 140 and a detector system 142 comprising an excitation source 144, an irradiation chamber 150 and a detector/analyzer 180. The irradiation chamber 150 including an excitation light port 152 in optical communication with the excitation source 144, and a fluorescent light port 154 having an optical filter 156 in optical communication with the detector/analyzer 180 and positioned in a direction making an angle with the excitation light to minimize or eliminate excitation light from entering the port 154. Generally, the angle is greater than or equal to ($\geq$) about 45°, preferably, the angle is greater than or equal to ($\geq$) about 60°, particularly, the angle is greater than or equal to ($\geq$) about 80°, and most particularly, the angle is substantially orthogonal to the excitation light port 152, i.e., 90°±5°. The irradiation chamber 150 also includes an oxidized sample inlet 158 and an oxidized sample outlet 160. The detector/analyzer 180 includes a photomultiplier tube (PMT) 182 for detecting fluorescent light and converting the detected light into an electrical output and an analyzer 184 for converting the PMT output into a measure of sulfur concentration in the original sample. The irradiation chamber 150 can also one or more mirrored interior surfaces or inserts having mirrored interior surfaces, where the mirrored surfaces are situated to 1) increase the amount of fluorescent light entering the port 154 and the PMT 182 and/or 2) to increase the amount of excitation light, such be chambers and inserts are described in U.S. Pat. No. 6,075,609 issued 13 Jun. 2000 and U.S. patent application Ser. No. 09/567,339 filed 9 May 2000, incorporated herein by reference.

Figure 1D:
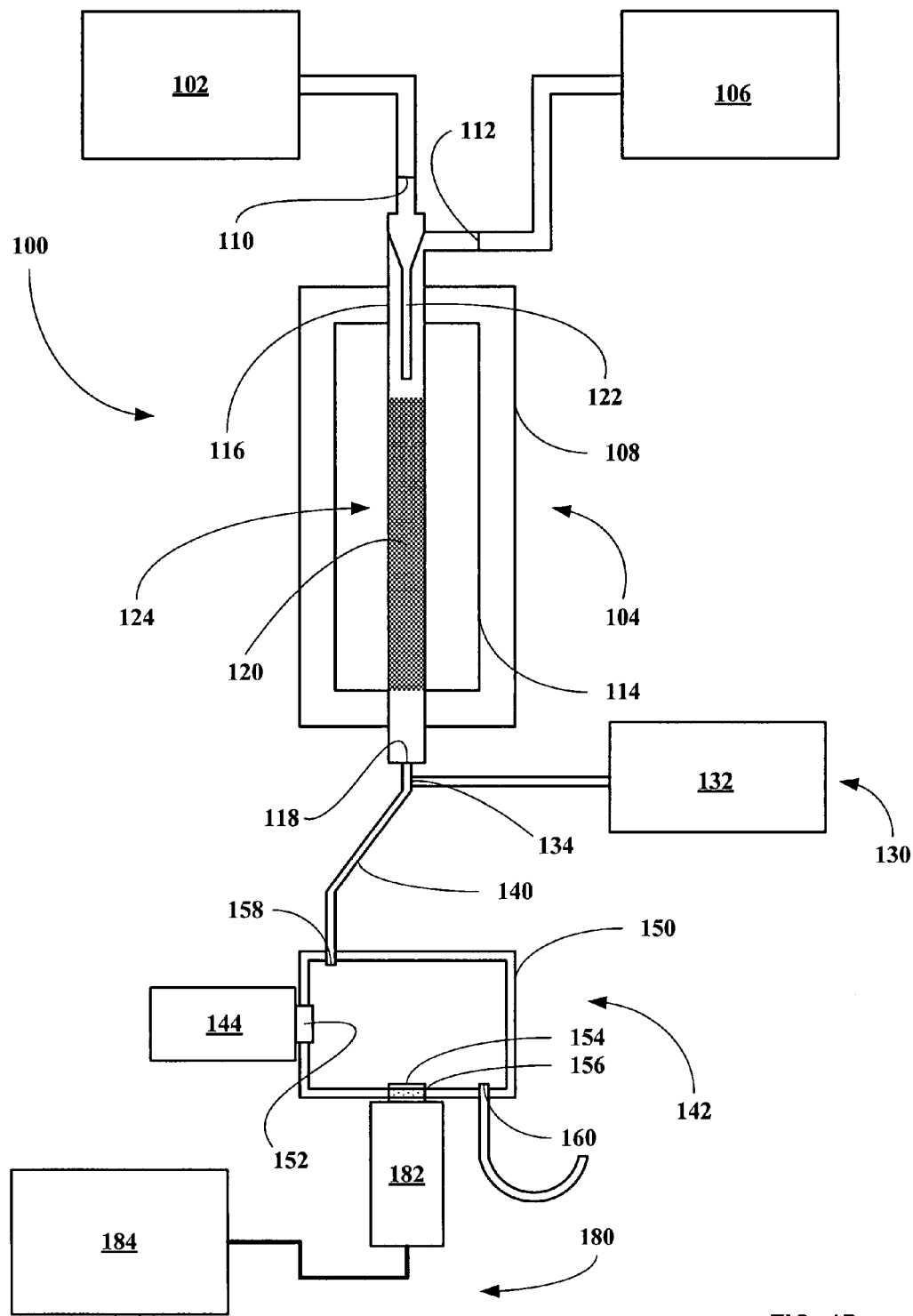
FIG. 1D depicts a block diagrams of another preferred embodiment of an apparatus of this invention including an UV interference reduction system comprising an ozone generator.

Referring now to FIG. 1D, another preferred embodiment of an instrument of this invention, generally 100, is shown to include a sample supply system 102 for introducing a sample into a combustion chamber 104 and an oxidizing agent supply 106 for introducing an oxidizing agent into the combustion chamber 104. The combustion chamber 104 includes a housing 108, a sample inlet 110, an oxidizing agent inlet 112, a heating element 114, a combustion tube 116 and an outlet 118. The combustion tube 116 can also include a packing 120 to improve oxidation efficient and a narrow inlet tube 122 adapted to atomize or nebulize the sample as it enters the combustion zone 124 of the combustion tube 116. The packing material can be any high temperature material such as glass chips, alumina chips, silica chips, silica alumina chips, or any shaped packing for increasing the surface area in the combustion zone. The instrument 100 also includes an UV interference reduction subsystem 130 comprising an ozone generator 132 and an ozone inlet 134 and a transfer tube 140 and a detector system 142 comprising an excitation source 144, an irradiation chamber 150 and a detector/analyzer 180, where the ozone is introduced into the transfer tube 140 near the outlet 118. The irradiation chamber 150 including an excitation light port 152 in optical communication with the excitation source 144, and a fluorescent light port 154 having an optical filter 156 in optical communication with the detector/analyzer 180 and positioned in a direction making an angle with the excitation light to minimize or eliminate excitation light from entering the port 154. Generally, the angle is greater than or equal to ($\geq$) about 45°, preferably, the angle is greater than or equal to ($\geq$) about 60°, particularly, the angle is greater than or equal to ($\geq$) about 80°, and most particularly, the angle is substantially orthogonal to the excitation light port 152, i.e., 90°±5°. The irradiation chamber 150 also includes an oxidized sample inlet 158 and an oxidized sample outlet 160. The detector/analyzer 180 includes a photomultiplier tube (PMT) 182 for detecting fluorescent light and converting the detected light into an electrical output and an analyzer 184 for converting the PMT output into a measure of sulfur concentration in the original sample. The irradiation chamber 150 can also one or more mirrored interior surfaces or inserts having mirrored interior surfaces, where the mirrored surfaces are situated to 1) increase the amount of fluorescent light entering the port 154 and the PMT 182 and/or 2) to increase the amount of excitation light, such be chambers and inserts are described in U.S. Pat. No. 6,075,609 issued 13 Jun. 2000 and U.S. patent application Ser. No. 09/567,339 filed 9 May 2000, incorporated herein by reference.

Figure 1E:
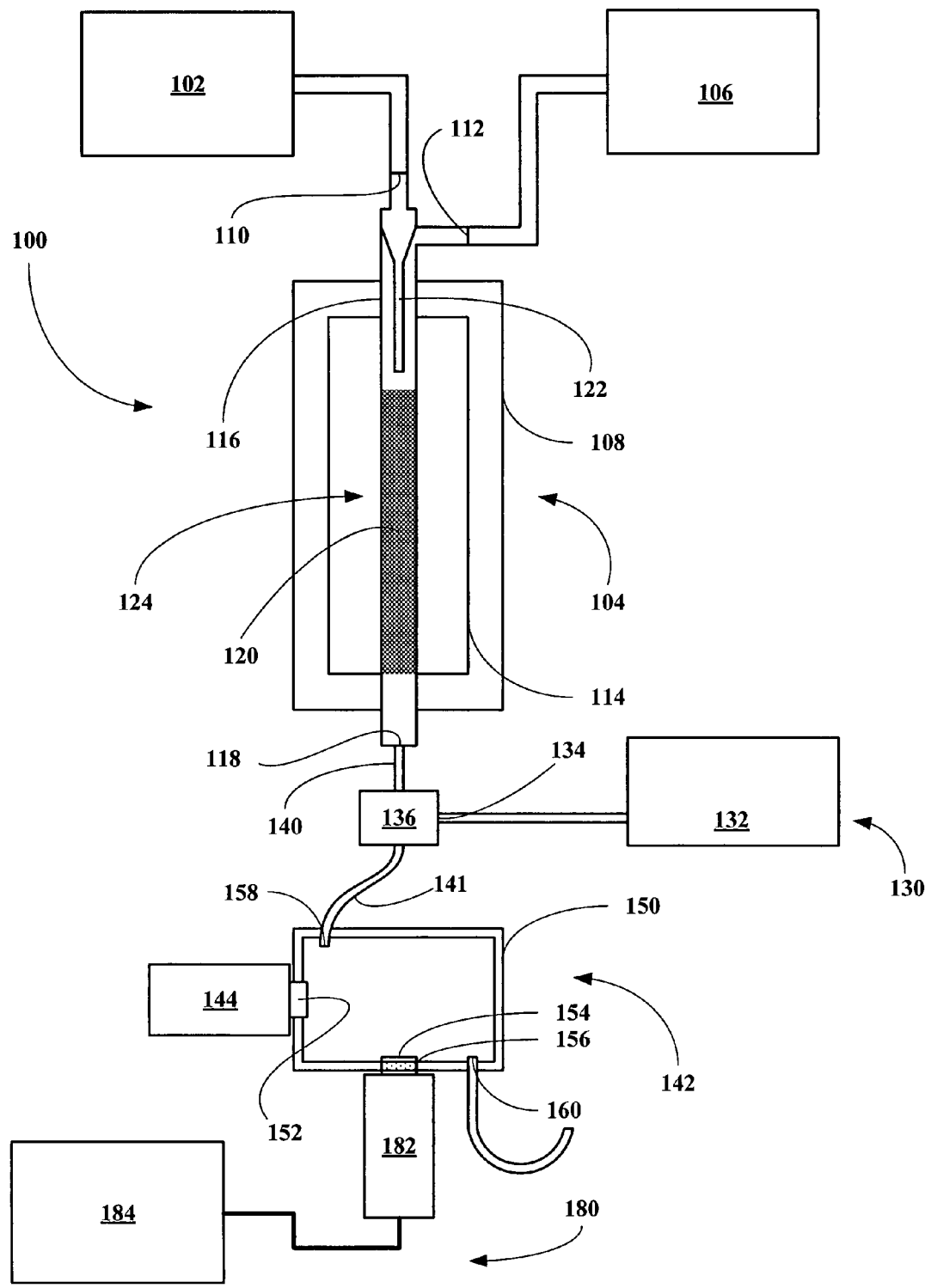
FIG. 1E depicts a block diagrams of another preferred embodiment of an apparatus of this invention including an UV interference reduction system comprising an ozone generator.

Referring now to FIG. 1E, another preferred embodiment of an instrument of this invention, generally 100, is shown to include a sample supply system 102 for introducing a sample into a combustion chamber 104 and an oxidizing agent supply 106 for introducing an oxidizing agent into the combustion chamber 104. The combustion chamber 104 includes a housing 108, a sample inlet 110, an oxidizing agent inlet 112, a heating element 114, a combustion tube 116 and an outlet 118. The combustion tube 116 can also include a packing 120 to improve oxidation efficient and a narrow inlet tube 122 adapted to atomize or nebulize the sample as it enters the combustion zone 124 of the combustion tube 116. The packing material can be any high temperature material such as glass chips, alumina chips, silica chips, silica alumina chips, or any shaped packing for increasing the surface area in the combustion zone. The instrument 100 also includes an UV interference reduction subsystem 130 comprising an ozone generator 132, an ozone inlet 134 and an ozone chamber 136 and a first transfer tube 140 and a second transfer line 141 and a detector system 142 comprising an excitation source 144, an irradiation chamber 150 and a detector/analyzer 180, where the ozone is introduced into the ozone chamber 136 upstream of the irradiation chamber 150. The irradiation chamber 150 including an excitation light port 152 in optical communication with the excitation source 144, and a fluorescent light port 154 having an optical filter 156 in optical communication with the detector/analyzer 180 and positioned in a direction making an angle with the excitation light to minimize or eliminate excitation light from entering the port 154. Generally, the angle is greater than or equal to ($\geq$) about 45°, preferably, the angle is greater than or equal to ($\geq$) about 60°, particularly, the angle is greater than or equal to ($\geq$) about 80°, and most particularly, the angle is substantially orthogonal to the excitation light port 152, i.e., 90°±5°. The irradiation chamber 150 also includes an oxidized sample inlet 158 and an oxidized sample outlet 160. The detector/analyzer 180 includes a photomultiplier tube (PMT) 182 for detecting fluorescent light and converting the detected light into an electrical output and an analyzer 184 for converting the PMT output into a measure of sulfur concentration in the original sample. The irradiation chamber 150 can also one or more mirrored interior surfaces or inserts having mirrored interior surfaces, where the mirrored surfaces are situated to 1) increase the amount of fluorescent light entering the port 154 and the PMT 182 and/or 2) to increase the amount of excitation light, such be chambers and inserts are described in U.S. Pat. No. 6,075,609 issued 13 Jun. 2000 and U.S. patent application Ser. No. 09/567,339 filed 9 May 2000, incorporated herein by reference.

Figure 1F:
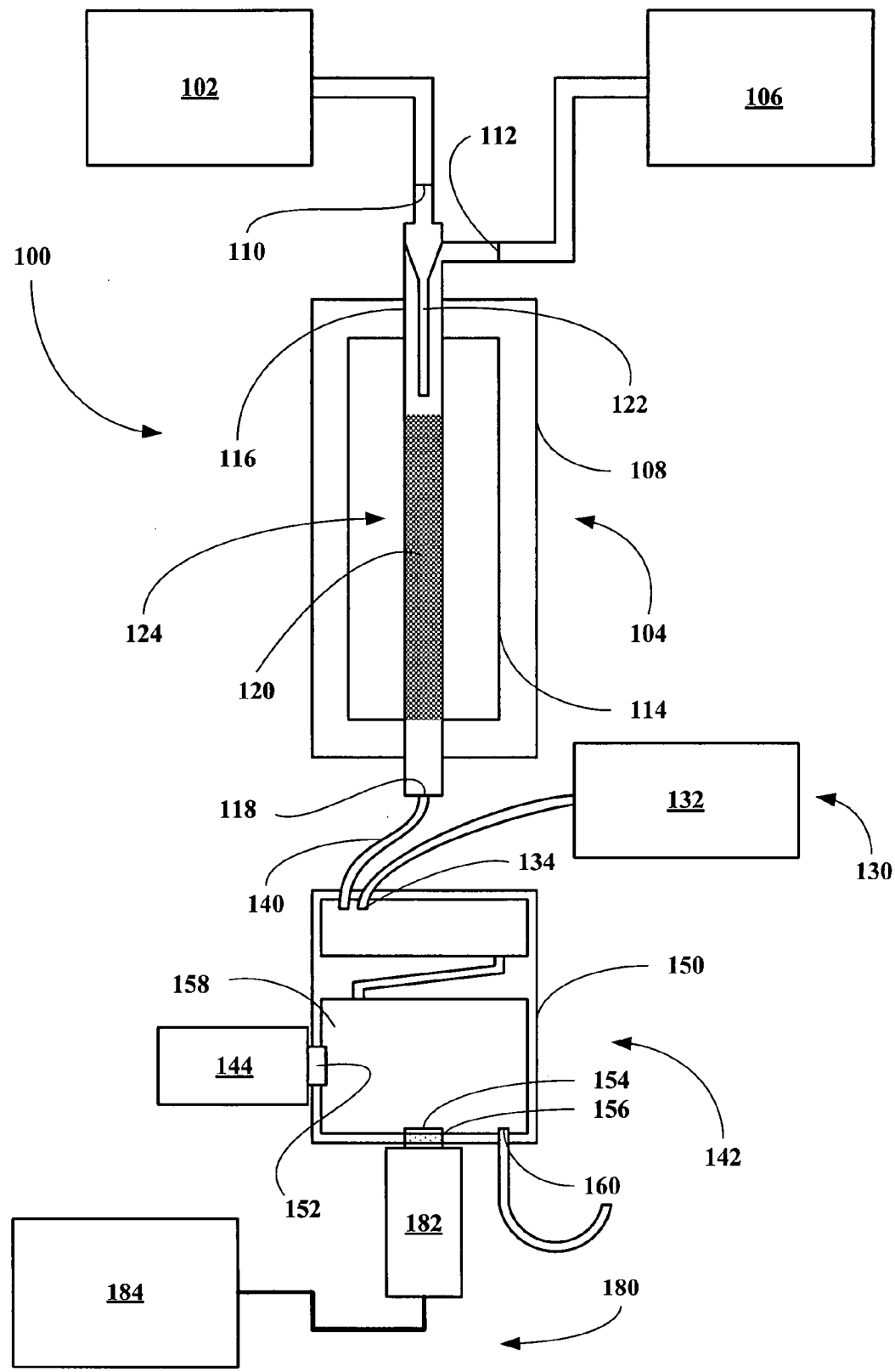
FIG. 1F depicts a block diagrams of another preferred embodiment of an apparatus of this invention including an UV interference reduction system comprising an ozone generator.

Referring now to FIG. 1F, another preferred embodiment of an instrument of this invention, generally 100, is shown to include a sample supply system 102 for introducing a sample into a combustion chamber 104 and an oxidizing agent supply 106 for introducing an oxidizing agent into the combustion chamber 104. The combustion chamber 104 includes a housing 108, a sample inlet 110, an oxidizing agent inlet 112, a heating element 114, a combustion tube 116 and an outlet 118. The combustion tube 116 can also include a packing 120 to improve oxidation efficient and a narrow inlet tube 122 adapted to atomize or nebulize the sample as it enters the combustion zone 124 of the combustion tube 116. The packing material can be any high temperature material such as glass chips, alumina chips, silica chips, silica alumina chips, or any shaped packing for increasing the surface area in the combustion zone. The instrument 100 also includes an UV interference reduction subsystem 130 comprising an ozone generator 132 and an ozone transfer tube 134 and a sample transfer tube 140 and a detector system 142 comprising an excitation source 144, a combined nitrogen oxide removal chamber and irradiation chamber 150 and a detector/analyzer 180. The nitrogen removal/irradiation chamber 150 includes an ozone reaction sub-chamber 136 and an excitation sub-chamber 151. The ozone reaction sub-chamber 136 includes an oxidized sample inlet 141 associated with the transfer line 140 and an ozone inlet 135 associated with the ozone transfer tube 134. The ozone sub-chamber also includes an oxidized sample outlet 139. The excitation sub-chamber 151 includes an excitation light port 152 in optical communication with the excitation source 144, and a fluorescent light port 154 having an optical filter 156 in optical communication with the detector/analyzer 180 and positioned in a direction making an angle with the excitation light to minimize or eliminate excitation light from entering the port 154. Additional bifurcated ozone chamber/excitation chamber designs can be found in U.S. Pat. Nos. 5,916,523 and 6,143,245, incorporated herein by reference, with the proviso that those chambers would have to include an excitation light port and a PMT port directed at an angle to the excitation light source.

Generally, the angle is greater than or equal to ($\geq$) about 45°, preferably, the angle is greater than or equal to ($\geq$) about 60°, particularly, the angle is greater than or equal to ($\geq$) about 80°, and most particularly, the angle is substantially orthogonal to the excitation light port 152, i.e., 90°±5°. The irradiation chamber 150 also includes an oxidized sample inlet 158 connected to the ozone chamber outlet 139 via a non-straight path 159 designed to reduce or eliminate chemiluminescent light produced in the ozone chamber from entering the excitation chamber 151 and an oxidized sample outlet 160. The detector/analyzer 180 includes a photomultiplier tube (PMT) 182 for detecting fluorescent light and converting the detected light into an electrical output and an analyzer 184 for converting the PMT output into a measure of sulfur concentration in the original sample. The irradiation chamber 150 can also one or more mirrored interior surfaces or inserts having mirrored interior surfaces, where the mirrored surfaces are situated to 1) increase the amount of fluorescent light entering the port 154 and the PMT 182 and/or 2) to increase the a mount o f excitation light, such be chambers and inserts are described in U.S. Pat. No. 6,075,609 issued 13 Jun. 2000 and U.S. patent application Ser. No. 09/567,339 filed 9 May 2000, incorporated herein by reference.

Figure 2:
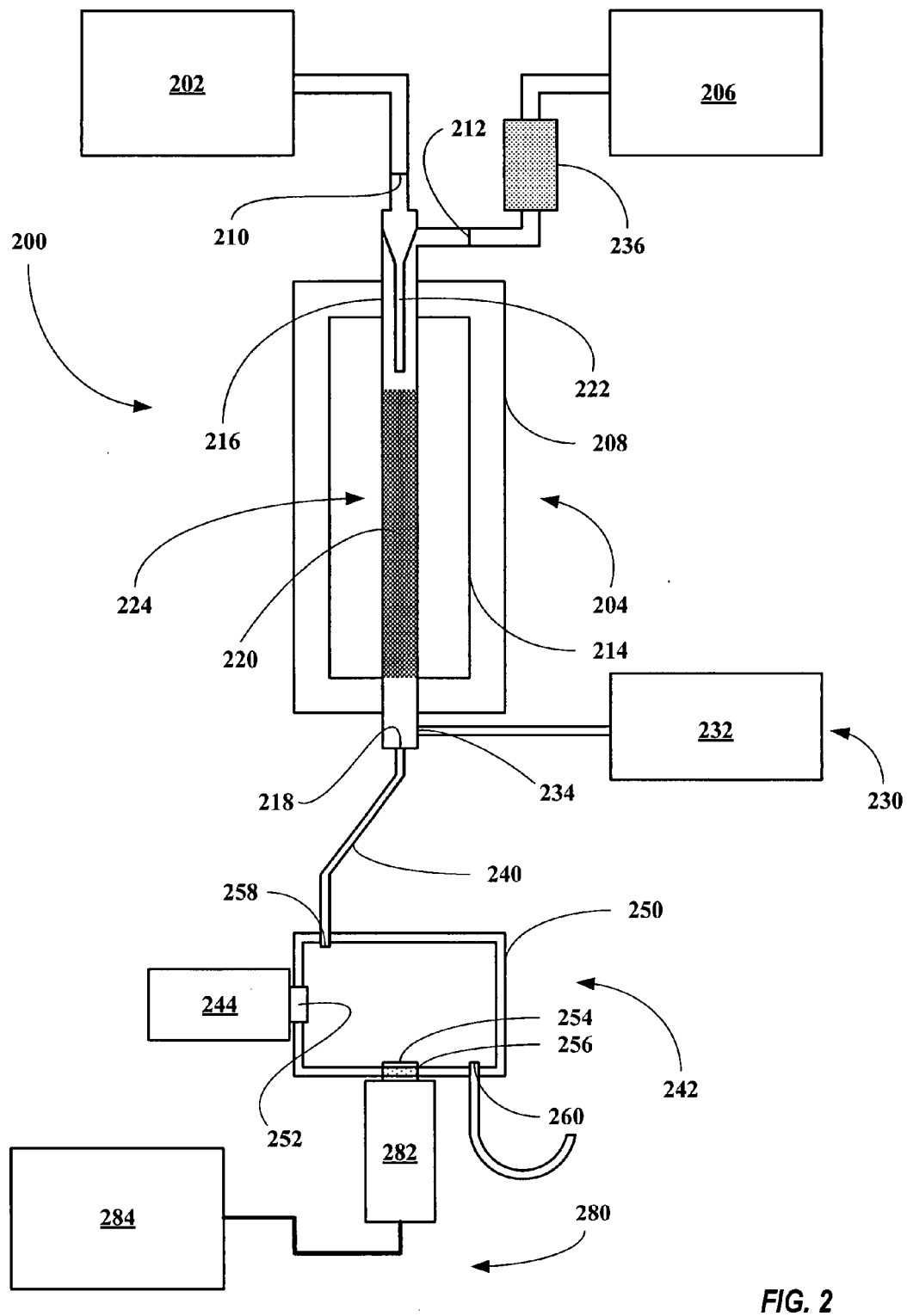
FIG. 2 depicts a block diagrams of another preferred embodiment of an apparatus of this invention including an UV interference reduction system comprising an ozone generator and a nitrogen filter.

Referring now to FIG. 2, another preferred embodiment of an instrument of this invention, generally 200, is shown to include a sample supply system 202 for introducing a sample into a combustion chamber 204 and an oxidizing agent supply 206 for introducing an oxidizing agent into the combustion chamber 204. The combustion chamber 204 includes a housing 208, a sample inlet 210, an oxidizing agent inlet 212, a heating element 214, a combustion tube 216 and an outlet 218. The combustion tube 216 can also include a packing 220 to improve oxidation efficient and a narrow inlet tube 222 adapted to atomize or nebulize the sample as it enters the combustion zone 224 of the combustion tube 216. The packing material can be any high temperature material such as glass chips, alumina chips, silica chips, silica alumina chips, or any shaped packing for increasing the surface area in the combustion zone. The instrument 200 also includes an UV interference reduction subsystem 230 comprising an ozone generator 232, an ozone inlet 234 introducing ozone into the combustion tube 216 near the outlet 218 and a nitrogen absorption filter 236 associated with the oxidizing agent supply 210. The instrument 200 also includes a transfer tube 240 and a detector system 242 comprising an excitation source 244, an irradiation chamber 250 and a detector/analyzer 280. The irradiation chamber 250 including an excitation light port 252 in optical communication with the excitation source 244, a fluorescent light port 254 having an optical filter 256 in optical communication with the detector/analyzer 280 and positioned substantially orthogonal to the excitation light port 252, an oxidized sample inlet 258 and an oxidized sample outlet 260. The detector/analyzer 280 includes a photomultiplier tube (PMT) 282 for detecting fluorescent light and converting the detected light to an electrical output and an analyzer 284 for converting the PMT output into a measure of sulfur concentration in the original sample. The irradiation chamber 250 also be a chamber as described in U.S. Pat. No. 6,075,609 issued 13 Jun. 2000 and U.S. patent application Ser. No. 09/567,339 filed 9 May 2000, incorporated herein by reference.

Although the above figures illustrate several preferred embodiments of instruments of this invention, it should be recognized that ozone can be added at more than one site in the instrument. Thus, ozone can be added with the oxidizing gas, near an exit of the combustion chamber, into the transfer line or into the detection system.

EXPERIMENTAL SECTION

Problem Definition

Conventional UV fluorescent instruments designed to analyze sulfur have for years been plagued with a response problem at very low sulfur levels, typically levels below about 100 ppb. These instruments have routinely given irreproducible results for low sulfur levels. Compounding this problem is the lack of agreement between UV fluorescent instruments and other sulfur detectors such as sulfur tape instruments when low sulfur standards are run. Generally, the tape instruments show sulfur contents for the standards well below the 50 ppb level, while UV fluorescent instruments often show sulfur contents for the same standards of 50 ppb or higher. Moreover, the problem are exacerbated when oxygen tanks are changed, joints leak and when other minor upsets to the system occur. Thus, a long felt need and uncured problem has plagued UV fluorescent instruments for low sulfur level detection.

Figure 3:
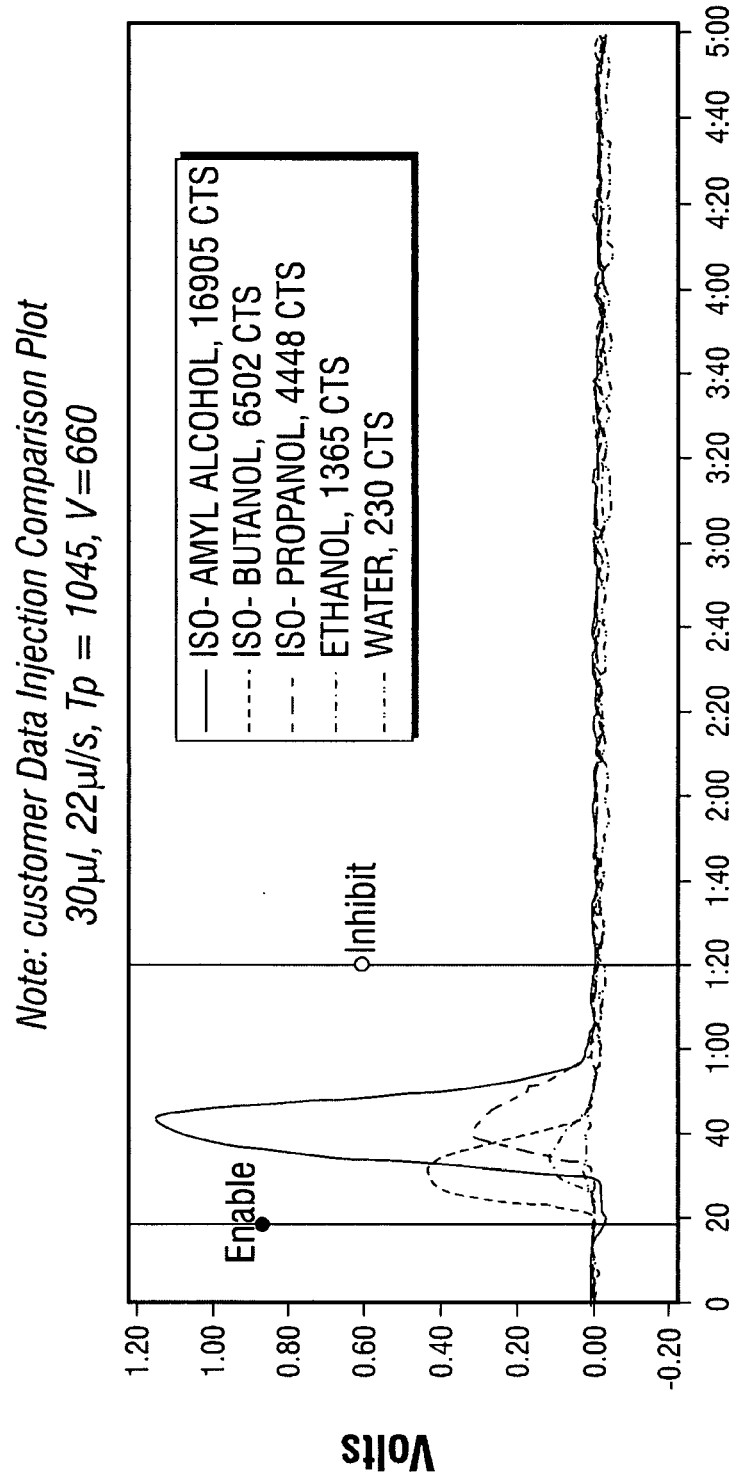
FIG. 3 depicts a graph of detector response verses a water and a series of alcohols using a conventional instrument, one without an UV interference reduction system.

The inventor of this invention solved this long felt need when confronted with the following data. A set of alcohols: ethanol, isopropanol, isobutanol and isoamyl alcohol were run on a conventional UV fluorescent instruments, one without an UV interference reduction system, with water used as the control. Referring now to FIG. 3, a plot of the responses of the set of alcohols vs. time is shown. Water showed essentially as zero peak having about 230 counts. Ethanol showed about 1365 counts, isopropanol showed about 4448 counts, iso-butanol showed about 6502 counts and iso amyl alcohol showed about 16905 counts. The inventor reasoned that a simple increase in molecular weight of the alcohols should not correlate with an increased amount of sulfur in the sample, especially for samples expected to have very low sulfur levels. Thus, the inventor reasoned that the effect (increased background signal) could not be related to molecular weight. The inventor reasoned that the background signal must be due to a contaminant. But what contaminant. The inventor noted that the heat of combustion for the alcohols increase with their molecular weight, therefore, the combustion temperature in oxygen will be higher for higher molecular weight alcohols. This fact lead the inventor to suspect that the contaminant may be being formed in the combustion product. Coupled with the fact that changing an oxygen bottle always produced a "background shift", the inventor speculated that the contaminant was a nitrogen oxide species formed during combustion.

To test this hypothesis, a sample of de-ionized water was analyzed and no measurable or detectable background peak was observed, confirming the data presented in FIG. 3 and observed independently by a customer of the assignee, Antek, LP. Next, responses from a series of five samples of 1 ppm S in iso-octane (i-C8 or iC8) and responses of five i-C8 standard samples were run to establish a baseline for subsequent comparison. Then, a sample containing 500 ppm by weight $N_2$ in deionized (DI) $H_2O$ was analyzed and found to respond about the same as an i-C8 sample containing 1.14 ppm S by weight. This data indicated about a 440:1 selectivity response, or "rejection ratio" between sulfur, as sulfur dioxide ($SO_2$) and an active nitrogen species, probably nitric oxide (NO). Methyl and isopropyl alcohols, as well as toluene were also analyzed during this test as a comparison. The data for each run is show in tabulated form in FIG. 4.

Figure 5:
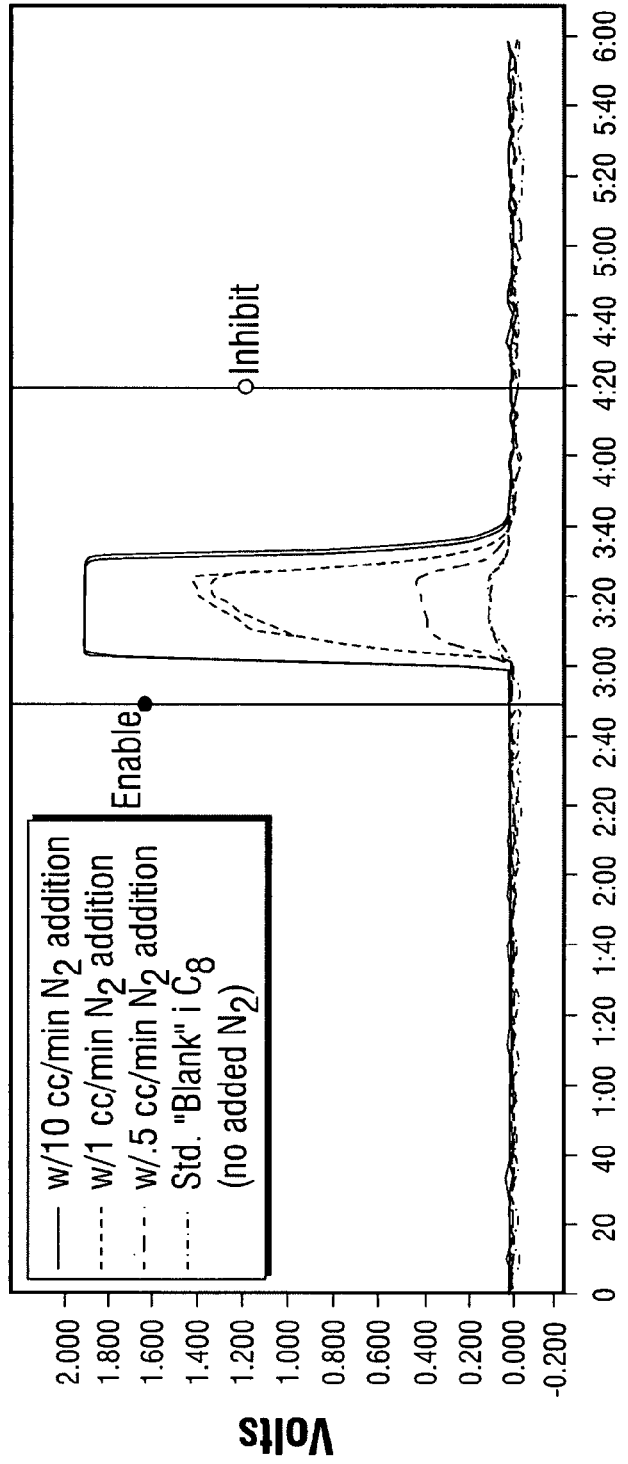
FIG. 5 depicts a graph of detector response verses a series of samples including different amount of nitrogen gas using an instrument without an UV interference reduction system.

Following the above tests, about 10 cc/min. of diatomic nitrogen ($N_2$) gas was added to the mixed Argon/Oxygen injector inlet and the response measure. The gas mixture yielded no detectable baseline shift when the $N_2$ was switched on and off. Thus, in the absence of a fuel and under normal furnace operating conditions where the furnace is maintained at between about 1050° C. and about 1100° C., oxidation of $N_2$ into nitrogen oxides does not occur. When an i-C8 standard samples were injected in the absence of added $N_2$ gas in the oxidizing gas mixture, only a small detector response was seen. However, when an i-C8 standard samples were injected in the presence of 10 cc/min. of $N_2$ gas in the oxidizing gas mixture, the detector response pegged off scale. Moreover, reducing the added $N_2$ gas flow, resulted in a corresponding reduction in the response of the i-C8 standard. The results of these runs are shown in FIG. 5. The fact that NO fluorescence can interfere with the detection of sulfur fluorescence is further evidenced the published work by Schwarz and Okabe. See F. P. Schwartz and H. Okobe, "Fluorescence Detection of Nitric Oxide in Nitrogen," *Anal. Chern.* 47,703 (1975). Schwarz and Okabe utilized the 214 nm line from a zinc lamp to excite NO resulting in an NO fluorescence spectrum between about 240 and about 310 nm for a 100 ppm NO in $N_2$ sample. This emission spectra lies within the instrument $SO_2$ fluorescence pass band filter of about 240 to about 400 nm. More recently, Olzewski and Zubek measured the NO fluorescence spectrum at substantially higher resolution (0.007A) utilizing an electron source with an impact excitation energy of 6.15 eV further showing that NO fluoresces within the pass band filter of conventional sulfur UV fluorescent instruments. See R. Olszewski and M. Zubek, "A Study of Electron Impact Excitation of A 21:+State of Nitric Oxide in the Near-Threshold Energy Range," *Chern. Phys. Lett.*, 340, 249, (2001).

The above data clearly shows that nitrogen oxides can interfere with sulfur detection using UV fluorescence detectors. There are two sources of nitrogen that can contribute to nitrogen oxide interference due to the production of NO during the oxidation of hydrocarbon containing samples. First, any nitrogen in the sample itself, such as chemically bound nitrogen or any nitrogen containing compound, is likely to interfere UV fluorescence methods directed to low level sulfur detection.

Second, regardless of any nitrogen in the sample itself, any $N_2$ in the oxygen, in the Argon, in any carrier gas and/or from incidental introductions of air upstream of the furnace such as during introduction of samples from a syringe or from leaks which could be converted to NO is likely to interfere UV fluorescence methods directed to low level sulfur detection.

The exact amount of $N_2$ converted to NO will of course depend on localized combustion temperature at or in excess of the temperature needed to oxidize $N_2$ (crack the N—N triple bond) into nitrogen oxides. Generally, the higher the carbon number, the more heat generated from combustion. The more heat generated the more $N_2$ oxidation and ultimately the more NO produced resulting in increased interference in sulfur detection. Clearly, this amount will be highly variable and substantially irreproducible. It is also clear that a combustible fuel is needed and a source of nitrogen is needed as water or simple gas mixtures show no detectable background as they contain either no nitrogen and do not generate any or sufficient heat to convert any $N_2$ present into nitrogen oxides such as NO.

Solutions

One approach to the reduction or elimination of interference from nitrogen oxides, especially, NO, in low level sulfur detection is to use ultra pure gas, e.g., ultra pure oxygen and ultra pure argon. However, even ultra pure oxygen and/or argon, which contain only trace, but variable, amounts of nitrogen gas, would only reduce, and not necessarily eliminate, the nitrogen interference in low level sulfur UV fluorescent detection. The approach will not necessarily eliminate nitrogen interference because it does not affect any nitrogen in the sample itself or nitrogen introduced into the combustion gases due to air leaks. Moreover, requiring the use of ultra pure gases is costly. Furthermore, use of ultra pure gas would likely require customers to have to switch gases whenever low level sulfur detection was desired, a significant inconvenience.

Another approach to reduce or eliminate interference from nitrogen oxides in low level sulfur UV fluorescence detection is to use a narrower fluorescence pass band filter in the detection chamber used to detect $SO_2$ fluorescence, where the narrower pass band filter would reduce or eliminate detection of NO fluorescent light. Unfortunately, narrowing the pass band filter would also significantly reduce $SO_2$ detector sensitivity and detection limits, a less than desirable outcome.

NO is naturally converted to $NO_2$, but at a relatively slow rate, in an oxidizing environment by the well established reaction:

$$NO+NO+O_2 \rightleftharpoons +NO_2+NO_2$$

Figure 6:
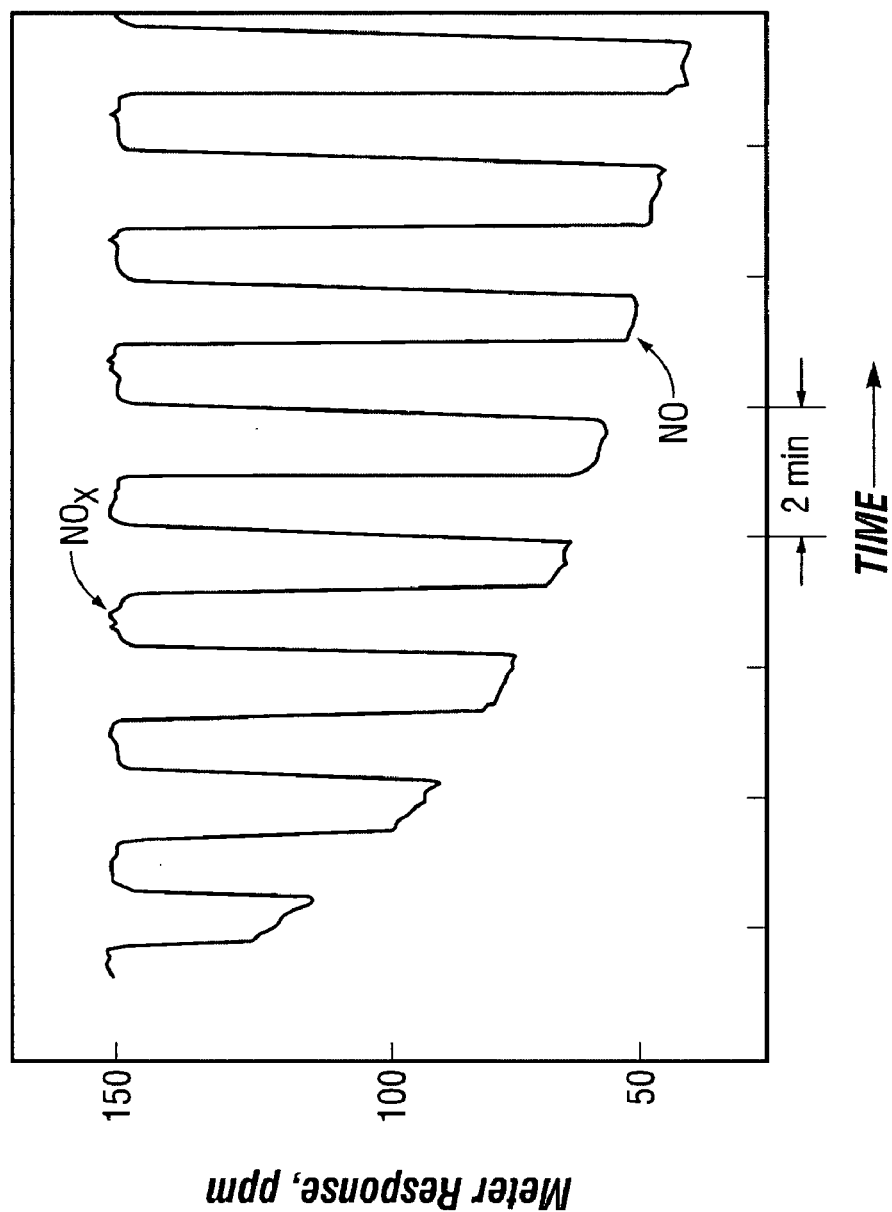
FIG. 6 depicts a graph of detector response verses $NO_x$ species during ozone induced chemiluminescence.
Figure 7A:
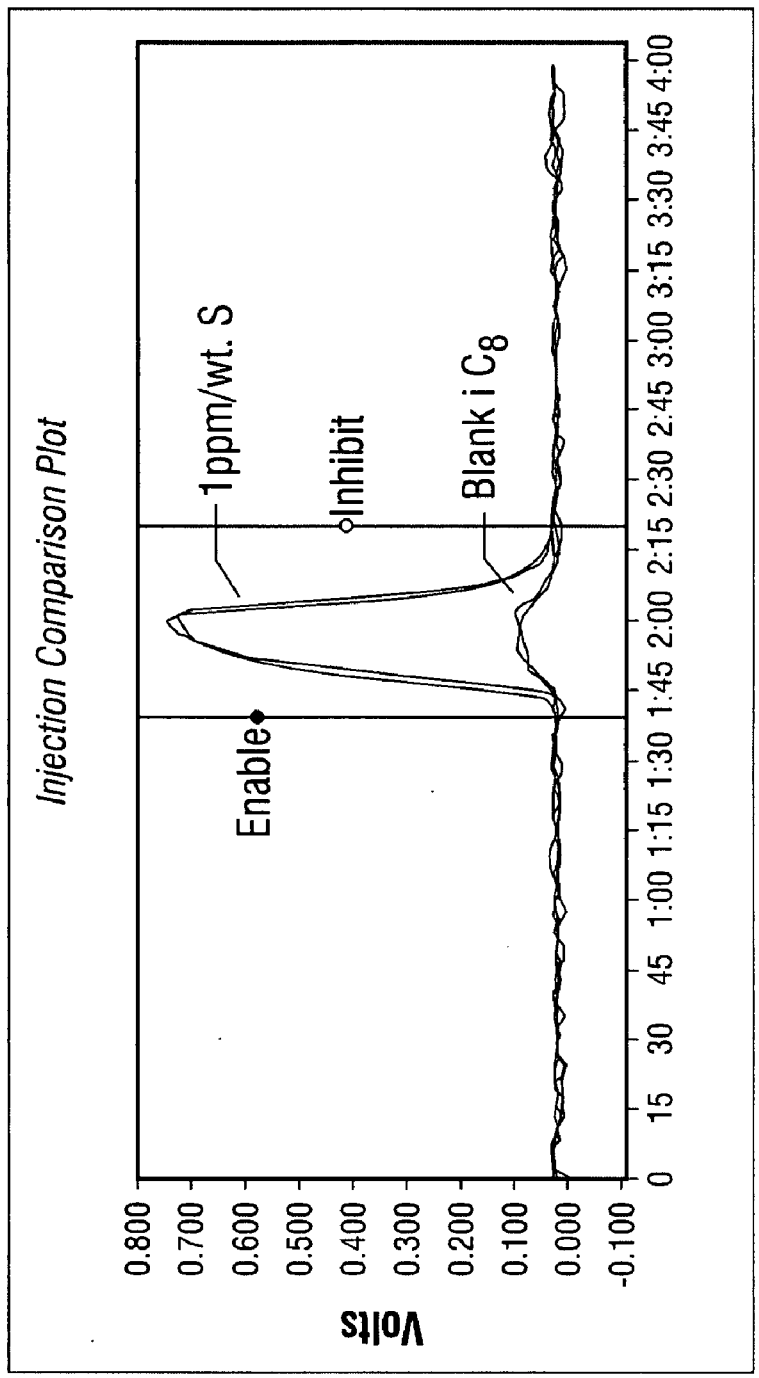
FIG. 7A depicts a graph of detector response verses a blank and an iso-octane sample containing 1 ppm sulfur using an instrument without an UV interference reduction system.
Figure 7B:
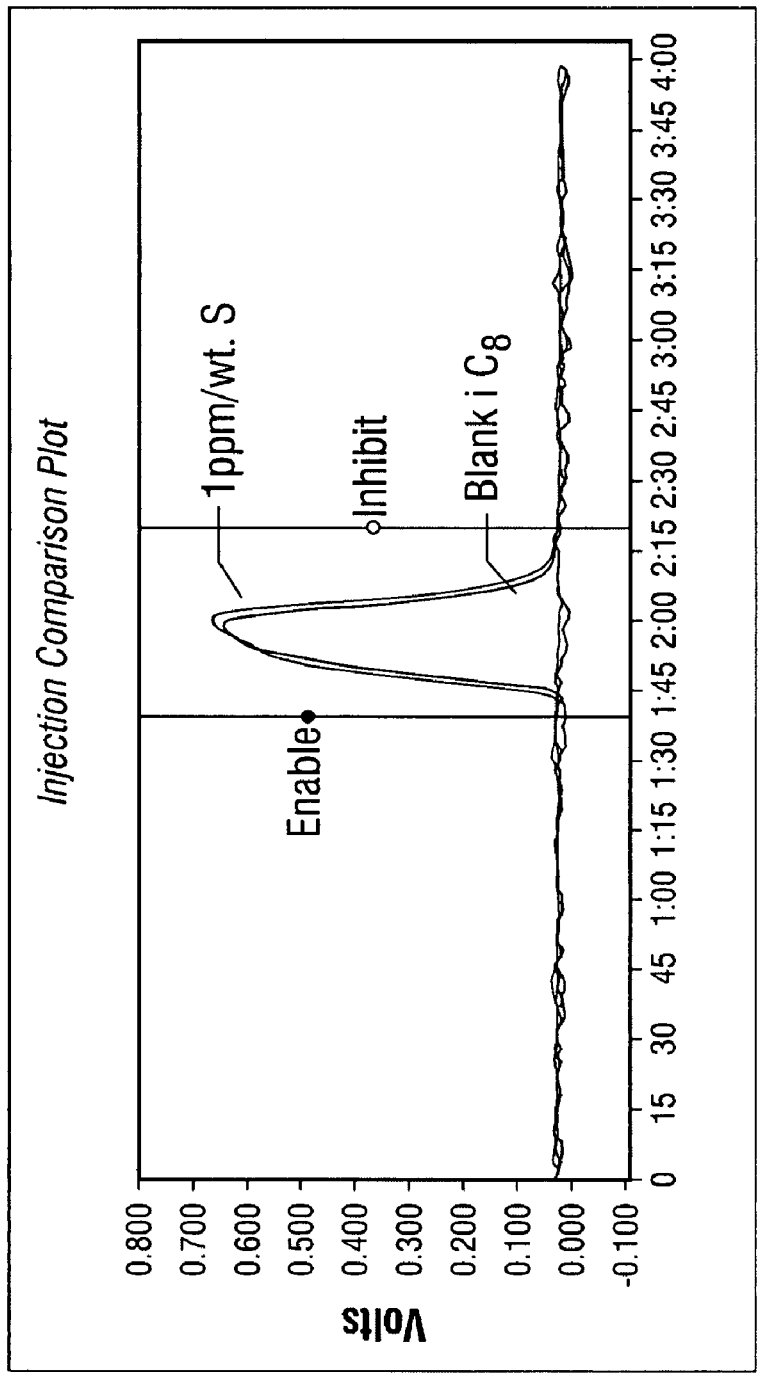
FIG. 7B depicts a graph of detector response verses a blank and an iso-octane sample containing 1 ppm sulfur using an instrument with an UV interference reduction system.

However, the reaction rate of 150 ppm NO in air has been previous found to have a half-life of about 5 minutes. Conversion at this rate is far too slow to be of any significant value to laboratory or on-line analytical instrumentation as shown in FIG. 6. Moreover, adjusting furnace conditions to favor $NO_2$ production is further hindered by the thermal conversion of $NO_2$ to NO at temperature at or above about 200° C., with a 50% conversion equilibrium established at about 600° C. according to the reaction:

$$2NO_2 \Leftrightarrow 2NO+O_2$$

Best Solutions

One preferred approach to reducing, minimizing or eliminating NO interference with low level sulfur UV fluorescence detection is to chemically convert NO to $NO_2$ before any formed NO reaches the UV fluorescence chamber. Chemical conversion of NO to $NO_2$ to reduce, minimize or eliminate NO interference can be accomplished by simply adding a non-interfering, NO conversion agent, prior to oxidation/combustion, during oxidation/combustion, after oxidation/combustion, but before detection, or during detection. Preferred NO conversion agents include, without limitations, ozone ($O_3$), hydrogen peroxide, or the like, with ozone being particularly preferred.

Ozone is known to react rapidly with NO to produce excited $NO_2$, a reaction exploited in nitrogen chemiluminescent analytical methods and instruments according to the following chemical reaction:

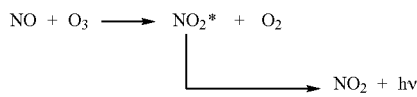

Although $NO_2$ has also been found to fluoresce, its emission spectrum generally lies in the visible region, predominantly outside of the $SO_2$ fluorescence spectrum. See, e.g., G. M. Myers, D. M. Silver and F. Kaufman, "Quenching of NO2 Fluorescence," *J. Chern. Phys.* 44,718 (1966) and K. Sakurai and H. B. Broida,"Spectral Study of $NO_2$ Fluorescence Excited by 11 Lines of Argon and Krypton Ion Lasers," *J. Chern. Phys.* 50,2404 (1969). Thus, converting NO to $NO_2$ means that the existing pass b and filter and PMT can be used in low-level sulfur UV fluorescence detection without compromising $SO_2$ sensitivity, while reducing or substantially eliminating NO fluorescent interference.

Ozone can be introduced into the system at any point such an into the oxidizing gas mixture, into the furnace via an additional inlet, anywhere downstream of the furnace, or into the detector system. Preferably, ozone is introduced after combustion, but sufficiently upstream of the detection chamber to reduce, minimize or eliminate any interference that may result from ozone induced NO chemiluminescence. However, ozone can be introduced directly into the detector, if the detector chamber is designed to reduce potential interference from ozone induce NO chemiluminescence. However, because ozone induced NO chemiluminescence should give rise only to a weak emission within the $SO_2$ fluorescence band, ozone may be able to be introduced directly in a conventional detection chamber without significant degradation in $SO_2$ detection sensitivity or detection limit. Moreover, the ozone induced NO chemilumines cence spectrum begins at or near the sensitivity "cut-off point" of the conventional PMT.

Although there may be certain potential adverse consequence of ozone addition to remove NO interference is low level sulfur UV fluorescence detection. These potentially adverse affects did not manifest themselves in the tests presented in this application. For completeness these potential adverse affects are discussed in turn.

First, light having a wavelength of about 410 nm or less is known to dissociate $NO_2$ back into NO through the reaction:

$$NO_2+hv \Rightarrow NO+O$$

but the rate of the reaction at wavelengths between about 210 nm and about 220 nm is unknown. However, recent experiments indicate that the reaction is either relatively slow, or there is sufficient excess $O_3$ to instantaneously convert any produced NO back into $NO_2$—no detectable background peaks were observed when ozone was added to the system. If $O_3$ does convert NO formed by the dissociated $NO_2$ back to $NO_2$ within the fluorescence cell, the emission must be too weak to detect.

Second, $O_3$ is known to absorb strongly in the deep UV and has recently been studied by Bogumil et at. See, K. Bogumil, J. Orphal, J. Burrows and J. M. Flaud, "Vibrational Progressions in the Visible and Near-Ultraviolet Absorption Spectrum of Ozone," *Chern. Phys. Lett.*, 349, 249, (2001). Although $O_3$ would absorb a smaller portion of the shorter wavelength $SO_2$ fluorescence emission, ozone would absorb a larger portion of UV excitation light, since the strongest ozone absorption band is between about 200 and about 300 nm with a peak at about 250 nm. This adverse effect was also not observed in the data present herein. However, it may be preferable to use an ozone generator capable of generating variable and adjustable concentrations of ozone instead of a constant valued ozone generator so that the ozone concentration can be adjusted to simultaneously minimize interfering NO fluorescent and minimize ozone absorption of excitation light and/or SO₂ fluorescence light during detection.

Referring now to FIGS. 7A-B and 8A-C, the results of a comparison of detector response of a conventional sulfur UV fluorescent instrument and an instrument including an ozone generator with the ozone introduced upstream of the detection chamber 150 or 250 as shown in FIGS. 1C-D and FIG. 2 are shown. Looking at FIG. 7A, a series of i-C8 standards were run resulting in small, but measurable background traces, Blank iC8. Next, a series of sample of i-C8 containing 1 ppm by weight S were run resulting in sulfur traces, 1 ppm/wt. S. Looking at FIG. 7B, a series of i-C8 standards were run in the presence ozone added to the furnace effluent upstream of the detection chamber resulting in essentially a stable baseline (no detectable signal), Blank iC8. Next, a series of sample of i-C8 containing 1 ppm by weight S were run in the presence ozone added to the furnace effluent upstream of the detection chamber resulting in sulfur traces, 1 ppm/wt. S. The ozone was generated by a variable ozone generator whose high-voltage output was adjusted to operate at a minimal breakdown or ozone producing voltage minimizing the amount of ozone produced. The response of 1 ppm, 50 ppb and blank i-C8 samples were analyzed for sulfur content both with and without ozone addition the results of which are tabulated in FIGS. 8A-C.

The above test indicated that with ozone addition, complete elimination of any detectable background response in the i-C8 standard could be obtained with little to no reduction in SO₂ response. However, less than expected response appears evident with the 50 ppb S samples where about a 30% or 15 ppb loss in sensitivity was noted even though the i-C8 standards are known to contain between about 20 and 30 ppb sulfur. Even with the reduction in apparent sensitivity in the 50 ppb samples and the lack of response due to the "unaccounted for" sulfur content of the standards, the response differences with and without ozone appeared linear and system repeatability was equal to or better with ozone than what is typically expected at these levels. These results clearly demonstrate the potential benefit of this improvement method and apparatus for low level sulfur UV fluorescence detection. Moreover, optimization of the amount of ozone and its point of addition will likely further improve low level sulfur detection. A summary of the results is given in Table I.

TABLE I

Preliminary Test Results of Nitrogen Interference Reduction by Ozone Addition

| Run | Reidel iC8 Std w/ O₃ | Fisher iC8 Std w/ O₃ | 50 ppb S in Fisher iC8 w/ O₃ | 1 ppm S in Fisher iC8 w/ O₃ | Fisher iC8 Std w/o O₃ | 50 ppb S in Fisher iC8 w/o O₃ | 1 ppm S in Fisher iC8 w/o O₃ |
|---|---|---|---|---|---|---|---|
| 1 | 37.6 | 28.6 | 429.9 | 9657.6 | 960.1 | 1133.6 | 11206.8 |
| 2 | 12.2 | 4.3 | 442.9 | 9871.8 | 919.6 | 1378.7 | 11363.2 |
| 3 | 28.1 | 0 | 287.1 | 9761.8 | 917.3 | 1321 | 11306.4 |
| 4 | 0.9 | 35.6 | 263.5 | 9815.8 | 1033.7 | 1107.7 | 11260.6 |
| 5 | 4.2 | 23 | 355.9 | 9974.7 | 986.9 | 1119.1 | 11417.8 |
| 6 | 0 | | 313.8 | | | | |
| 7 | 6.4 | | 317.1 | | | | |
| 8 | 5.1 | | 337.3 | | | | |
| 9 | 2.2 | | 370.6 | | | | |
| 10 | 14.4 | | 425.4 | | | | |
| 11 | | | 245.3 | | | | |
| 12 | | | 363.7 | | | | |
| 13 | | | 270.8 | | | | |
| 14 | | | 414.5 | | | | |
| 15 | | | 369.2 | | | | |
| Average | 11.11 | 18.30 | 355.86 | 9816.34 | 963.52 | 1212.02 | 11310.96 |
| Std. Dev | 12.54 | 15.48 | 62.33 | 118.67 | 48.86 | 127.79 | 82.99 |
| % Rel. | 112.88 | 84.58 | 17.51 | 1.21 | 5.07 | 10.54 | 0.73 |
| 50 ppb* | | | 337.56 | | | 248.50 | |
| 1 ppm* | | | | 9798.04 | | | 10347.44 |

*Average value minus average value of blank

*The data clearly demonstrates that nitrogen oxides interfere with low level sulfur UV fluorescence and that the addition of ozone can reduce and/or eliminate the interference. Although there appears to be a reduction in single for very low level sulfur, optimization of ozone introduction and ozone level may improve lower limit detection threshold. Moreover, the removal of interfering nitrogen oxide fluorescence greatly improves stability, reproducibility and reliability of low level sulfur detection by UV fluorescent spectrometry.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that maybe made which do not depart from the scope and spirit of the invention as described above and claimed hereafter.

I claim:

1. An apparatus for performing low level sulfur UV fluorescence detection comprising:
   an oxidation or combustion chamber including:
   a sample inlet,
   an oxidizing agent inlet,
   an oxidation zone, and
   an oxidized sample outlet,
   where the oxidation chamber is adapted to convert substantially all oxidizable components of a sample into their corresponding oxides;

a transfer tube connected to the oxidized sample outlet adapted to transfer the corresponding oxides to an UV chamber;

an UV interference reduction system adapted to introduce an UV interference reduction agent into the sample before during and/or after oxidation, where the UV interference reduction agent is capable of reducing or eliminating nitrogen oxides that interfere with sulfur UV fluorescence detection; and a detector/analyzer system including:
an excitation light source adapted to generate excitation light,
the UV chamber having:
an excitation light port in optical communication with the light source adapted to excite $SO_2$ molecules in the oxidized sample into electronically excited $SO_2$ molecules,
an oxidized sample inlet connected to the transfer tube,
an oxidized sample outlet for exhausting the oxidized sample from the chamber after irradiation from the excitation light, and
a fluorescent light port oriented at an angle to the excitation light port, where the angle is sufficient to reduce or eliminate excitation light from entering the fluorescent light port;
a fluorescent light detector in optical communication with the fluorescent light port adapted to detect fluorescent light emitted by the electronically excited $SO_2$ molecules passing through the fluorescent light port and to convert the detected fluorescent light into an electrical output signal, and
an analyzer in electrical communication with the detector and adapted to convert the electrical output signal into a concentration of sulfur in the sample,
where the UV interference reduction agent is introduced in an amount sufficient to convert interfering nitrogen oxides into non-interfering nitrogen oxides thereby lowering a sulfur detection limit to sulfur concentrations of less than 100 ppb.

2. The apparatus of claim 1, further comprising:
a nitrogen filter connected to the oxidizing agent inlet to remove trace amounts of nitrogen gas ($N_2$) in the oxidizing gas prior to the oxidizing agent entering the oxidizing agent inlet of the combustion chamber.

3. The apparatus of claim 1, wherein the UV interference reduction agent comprises a nitric oxide reactive species selected from the group consisting of ozone and hydrogen peroxide.

4. The apparatus of claim 1, wherein the amount of the UV interference reduction agent is sufficient to lower the sulfur detection limit to sulfur concentrations below 50 ppb.

5. The apparatus claim 1, wherein the UV chamber further includes:
an optical filter associated with the fluorescent light port and
wherein the fluorescent light detector comprises a photomultiplier tube (PMT).

6. The apparatus of claim 1, wherein the oxidizing agent comprises an oxygen containing gas selected from the group consisting of oxygen, oxygen in argon, ultra-pure oxygen, ultra-pure oxygen in argon, or ultra-pure oxygen in ultra-pure argon.

7. The apparatus of claim 1, wherein the UV interference reduction system comprises:
an ozone generator and
wherein the UV interference reduction agent comprises ozone.

8. The apparatus of claim 7, wherein the ozone is introduced into the oxidizing agent inlet of the combustion chamber.

9. The apparatus of claim 7, wherein the ozone is introduced into the oxidizing zone through an ozone inlet.

10. The apparatus of claim 7, wherein the ozone is introduced into the combustion chamber at its distal end through an ozone inlet.

11. The apparatus of claim 7, wherein the ozone is introduced into the transfer tube through an ozone inlet.

12. The apparatus of claim 7, wherein the transfer tube includes:
an ozone chamber having an ozone inlet and
wherein the ozone is introduced into the ozone chamber through the ozone inlet.

13. The apparatus of claim 7, wherein the UV chamber further includes:
a first sub-chamber having an ozone inlet and
wherein the ozone is introduced into the first sub-chamber through the ozone inlet.

14. The apparatus of claim 7, wherein the ozone generator generates variable concentrations of ozone to simultaneously minimize interfering nitric oxide fluorescence and ozone absorption of excitation light and/or $SO_2$ fluorescent in the UV chamber.

* * * * *